United States Patent
Mitachi et al.

(10) Patent No.: US 9,420,964 B2
(45) Date of Patent: Aug. 23, 2016

(54) OPTICAL FIBER SHEET AND BODY MOTION SENSOR

(75) Inventors: Seiko Mitachi, Kunitachi (JP); Toshifumi Hosoya, Osaka (JP); Kazuhiro Kuwa, Osaka (JP)

(73) Assignees: Sumitomo Electric Industries, Ltd., Osaka-shi (JP); Seiko Mitachi, Kunitachi-shi (JP)

(*) Notice: Subject to any disclaimer, the term of this patent is extended or adjusted under 35 U.S.C. 154(b) by 644 days.

(21) Appl. No.: 13/259,120

(22) PCT Filed: Mar. 24, 2010

(86) PCT No.: PCT/JP2010/055037
§ 371 (c)(1), (2), (4) Date: Dec. 7, 2011

(87) PCT Pub. No.: WO2010/110292
PCT Pub. Date: Sep. 30, 2010

(65) Prior Publication Data
US 2012/0070112 A1    Mar. 22, 2012

(30) Foreign Application Priority Data
Mar. 25, 2009 (JP) .................. 2009-074331

(51) Int. Cl.
A61B 5/113 (2006.01)
G01D 5/353 (2006.01)
A61B 5/00 (2006.01)

(52) U.S. Cl.
CPC ........... *A61B 5/113* (2013.01); *A61B 5/4818* (2013.01); *A61B 5/6892* (2013.01);
(Continued)

(58) Field of Classification Search
CPC .............................. A61B 2562/0266
See application file for complete search history.

(56) References Cited

U.S. PATENT DOCUMENTS 4,342,907 A * 8/1982 Macedo et al. .......... 250/227.14
4,359,726 A   11/1982 Lewiner et al.
(Continued)

FOREIGN PATENT DOCUMENTS

CN    1665442 A    9/2005
CN    1933777 A    3/2007
(Continued)

OTHER PUBLICATIONS

Office Action in Chinese Patent Application No. 201080013603.5 dated Apr. 16, 2013.
(Continued)

*Primary Examiner* — Michelle R Connelly
(74) *Attorney, Agent, or Firm* — Venable LLP; Michael A. Sartori; Tamatane J. Aga (57) ABSTRACT

A body motion sensor, such as an SAS diagnostic device, with which a subject can be examined in a state close to that in an ordinary living environment and it is possible to clearly discriminate between an apnea state and a hypopnea state by means of a relatively simple analytical method; and an optical fiber sheet suitable for use in the sensor. The body motion sensor, such as an SAS diagnostic device, comprises a light source such as an LED, an optical fiber sheet, and an analysis unit that determines fluctuations in the quantity of light outputted from the optical fiber sheet and detects motions of the body. As the optical fiber sheet, use is made of an optical fiber sheet comprising a planar object, such as a fabric, paper, or plastic sheet, and graded-index optical quartz fibers directly or indirectly disposed thereon or affixed thereto When the sheet is produced, it is preferred to use a pressure-sensitive adhesive sheet comprising a sheet support, such as paper or fabric, and a pressure-sensitive adhesive layer formed thereon.

9 Claims, 9 Drawing Sheets

(52) U.S. Cl.
CPC ....... G01D 5/35303 (2013.01); G01D 5/35345 (2013.01); *A61B 2562/0247* (2013.01); *A61B 2562/0266* (2013.01); *Y10T 156/10* (2015.01)

(56) References Cited

U.S. PATENT DOCUMENTS

| | | | |
|---|---|---|---|
| 5,212,379 | A | 5/1993 | Nafarrate et al. |
| 6,415,167 | B1 | 7/2002 | Blank et al. |
| 6,434,309 | B1* | 8/2002 | Abbott et al. .................. 385/123 |
| 6,456,381 | B1* | 9/2002 | Nakamura et al. ............ 356/483 |
| 6,498,652 | B1* | 12/2002 | Varshneya et al. ............ 356/477 |
| 6,788,397 | B1* | 9/2004 | Golowich et al. ............. 356/121 |
| 7,196,317 | B1* | 3/2007 | Meissner et al. ......... 250/227.14 |
| 7,423,279 | B2* | 9/2008 | Heinz et al. ............... 250/559.32 |
| 8,195,013 | B2* | 6/2012 | Lagakos et al. ................. 385/12 |
| 8,926,143 | B2* | 1/2015 | Li et al. .................... 362/311.02 |
| 2004/0021255 | A1 | 2/2004 | Bilanin et al. |
| 2007/0037462 | A1 | 2/2007 | Allen et al. |
| 2008/0064964 | A1 | 3/2008 | Nagata et al. |
| 2008/0221488 | A1 | 9/2008 | Kurono et al. |
| 2008/0253712 | A1* | 10/2008 | Allen et al. ...................... 385/12 |
| 2009/0252451 | A1* | 10/2009 | Lagakos et al. ................. 385/13 |
| 2010/0134236 | A1 | 6/2010 | Hatsuda |

FOREIGN PATENT DOCUMENTS

| | | |
|---|---|---|
| CN | 100998501 A | 7/2007 |
| JP | 3-210440 A | 9/1991 |
| JP | 04-204114 A | 7/1992 |
| JP | 05-200001 A | 8/1993 |
| JP | 2001-074607 A | 3/2001 |
| JP | 2002-081192 A | 3/2002 |
| JP | 2002-219108 A | 8/2002 |
| JP | 2005-532854 A | 11/2005 |
| JP | 2007-061306 A | 3/2007 |
| JP | 2007-144070 A | 6/2007 |
| JP | 2008-284001 A | 11/2008 |
| WO | WO-2004/006768 A1 | 1/2004 |
| WO | WO-2009/013981 A1 | 1/2009 |

OTHER PUBLICATIONS

Search Report in European Patent Application No. 10756088.0-1657, dated Mar. 26, 2013.
Gorodetzky, P. et al., "Quartz fiber calorimetry," Nuclear Instruments & Methods in Physics Research, Section A, vol. A361, No. 1, Jul. 1, 1995, pp. 161-179.
Notice of Grounds of Rejection issued in Japanese Patent Application No. 2011-506073 dated Feb. 9, 2015.

* cited by examiner

OPTICAL FIBER SHEET AND BODY MOTION SENSOR

TECHNICAL FIELD

The present invention relates to an optical fiber sheet and a body motion sensor. More specifically, it relates to a body motion sensor suitably employed for diagnosing sleep apnea syndrome and an optical fiber sheet suitable for the sensor.

BACKGROUND ART

Triggered by the report of the drowsy driving on the Shinkansen in 2003, sleep apnea syndrome (SAS) has rapidly attracted a great deal of attention in recent years. SAS is a disease in which such a symptom that respiration stops (apnea state) for at least 10 seconds or the respiratory tract is narrowed to thin the respiration while the patient sleeps, more specifically, the amount of ventilation lowers (hypopnea state) by at least 50% for at least 10 seconds is repeated at least five times an hour on the average. Symptoms such as a headache in getting up and drowsiness in the daytime appear in the SAS patient. SAS also causes hypertension, and it is said that the rate of complication of a myocardial infarction, cerebral apoplexy and the like rises in the SAS patient. In addition, symptoms such as nycturia, impotence, heaviness in the head and hydrodipsia may also appear. While SAS is frequently observed among middle-aged and elderly males, it is said that the same has been on the increase also among children in recent years. While the cause therefor is unknown, it is also said that the same is the fate of the human race getting to so frequently ingest soft food that the chin begins to degenerate.

It is said that the number of SAS patients is about 4% of the total population, i.e., 4.8 million in number in Japan, and it is also said that the number of potential patients thereamong is 2.8 million. An SAS patient tends to cause a traffic accident or an industrial accident by drowsy driving. It is extremely dangerous for an SAS patient to work as the driver of public transport such as an electric train, and an immediate countermeasure is required.

In the meantime, SAS is mainly diagnosed by precise diagnosis with a polysomnogram test (PSG test) at present, and a simple method omitting partial items of the PSG test, such as a simple test employing a pulse oximeter or a respiratory frequency (respiration rate) measurer, for example, is utilized as a screening method. While the subject can be tested with a portable apparatus and may not be hospitalized but can be tested also at home in the simple test, the PSG test is necessary for definition of the diagnosis. In the diagnosis with the PSG, however, hospitalization is regarded as necessary. Further, analysis by a technician is necessary after the test, and labor, time and high cost have been required. In the PSG test or the simple test, in addition, a measuring tool such as a thermistor is arranged around the mouth or the nose of the subject, and hence the same has disturbed a natural sleep.

On the other hand, a method of examining the presence or absence of respiration through a body motion resulting from respiration has also been developed. For example, a method employing a specific mat for catching a change in the height of the mat resulting from respiration as a change in the air pressure has been put into practice. However, this method is inferior in SN ratio. In other words, this method is a technique of determining the change from specific mathematical signal analysis in order to distinguish a body motion resulting from a pulse or turning over while sleeping in bed and a body motion resulting from respiration from each other, and has been inferior in reliability. Further, an apparatus for detecting the change in the air pressure must be incorporated into the mat, and hence the structure is complicated, and manufacturing thereof has also been intricate.

Under such circumstances, an optical fiber sheet prepared by fixing or mixing optical fiber to or into a sheet or the like made of cloth or the like is disclosed in Japanese Patent Laying-Open No. 2007-61306. This optical fiber sheet catches a shape change in the optical fiber caused by a body motion as a change in a polarization state of light propagating in the optical fiber. In a case of employing this optical fiber sheet, there are such advantages that the SN ratio is excellent, a slight body motion such as respiration can be detected, turning over while sleeping in bed or a pulse and respiration can be clearly distinguished from each other, and the state of respiration can be observed in a state close to an ordinary living environment.

CITATION LIST

Patent Literature

PTL 1: Japanese Patent Laying-Open No. 2007-61306

SUMMARY OF INVENTION

Technical Problem

However, the aforementioned optical fiber sheet catches the body motion as the quantity of fluctuation in the polarization state of the light. In order to measure this quantity of polarization fluctuation, a specific analytical apparatus analyzing the light emitted from the optical fiber is required, and professional ability is required for the analysis. Further, the optical fiber for measuring the polarization fluctuation employed in Patent Document 1 has an anisotropic sectional shape and the quantity of polarization fluctuation has bending dependence, and hence there is such a problem that sensitivity to the body motion fluctuates every sheet unless the sheet is formed to catch a direction sensitive to the fluctuation.

An object of the present invention is to provide a body motion sensor capable of testing a subject in a state close to an ordinary living environment and capable of clearly distinguishing an apnea state and a hypopnea state from each other by correctly sensing a body motion with a relatively simple analytical method.

Solution to Problem

An optical fiber sheet according to the present invention is an optical fiber sheet including optical fiber and a planar body, for measuring a change in the quantity of transmission signal light based on excess loss caused by a lateral pressure applied to the optical fiber, characterized in that the said optical fiber is graded index quartz-based optical fiber.

The graded index quartz-based optical fiber (hereinafter referred to as GI quartz-based optical fiber) is employed for the optical fiber sheet according to the present invention. The GI quartz-based optical fiber causes microbending loss by stress loading resulting from a lateral pressure, and excess loss is caused in transmission loss of the optical fiber. The present invention has rendered a body motion detectable by measuring a change in the quantity of transmission signal light based on this excess loss. The GI quartz-based optical fiber has large excess loss resulting from a lateral pressure, and hence a remarkable light quantity change is measured through a slight body motion change. Therefore, an apnea state and a hypopnea state between which no remarkable difference in body motion is observed can be clearly distinguished from each other.

A method of manufacturing an optical fiber sheet according to the present invention has a step of fixing GI quartz-based optical fiber to an adhesive sheet including an adhesive layer on a planar body. According to this method, the optical fiber can be fixed to the planar body by simply arranging the optical fiber on the adhesive sheet. Consequently, productivity of the optical fiber sheet improves.

Advantageous Effects of Invention

In the present invention, information on turning over while sleeping in bed or a pulse unnecessary for diagnosis of SAS and respiration information necessary therefor can be clearly distinguished from each other with only simple analysis of measuring a change in the quantity of light output from the optical fiber sheet.

DESCRIPTION OF EMBODIMENTS

An optical fiber sheet according to the present invention is an optical fiber sheet including optical fiber and a sheetlike body for measuring a change in the quantity of transmission signal light based on excess loss caused by a lateral pressure applied to the optical fiber, and characterized in that the said optical fiber sheet is graded index quartz-based optical fiber. This optical fiber sheet is suitably employed for an SAS diagnostic apparatus for diagnosing sleep apnea syndrome from a body motion or the like, for example. The present invention is now described in detail with reference to the attached drawings.

EXAMPLE 1

Figure 1:
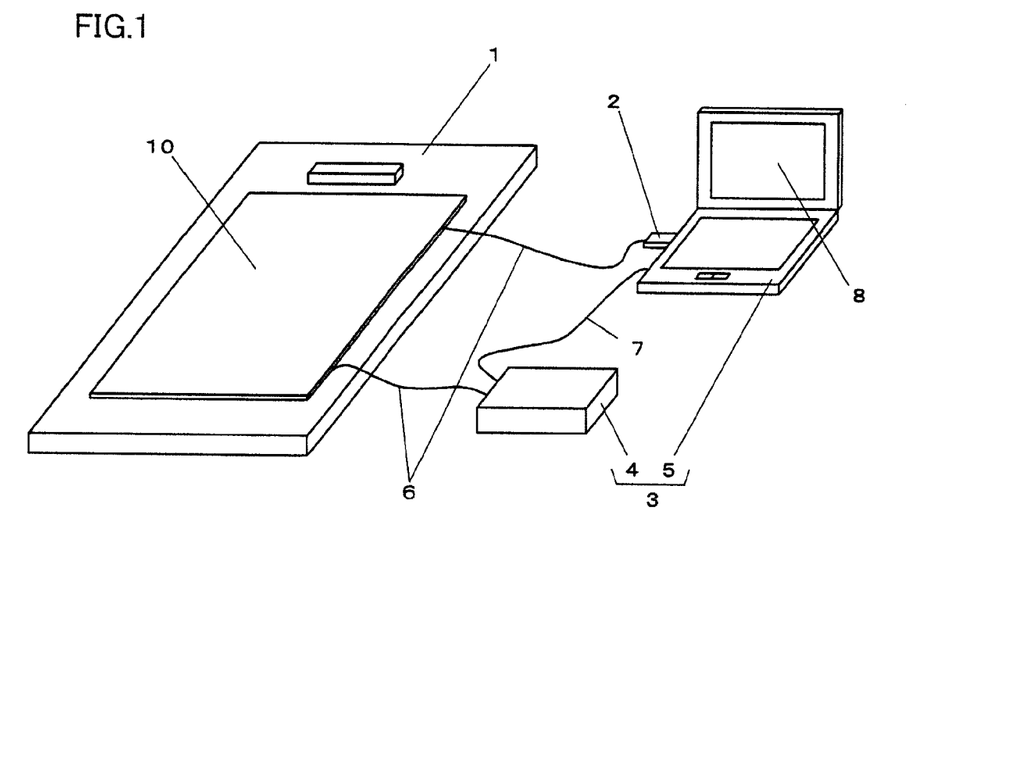
FIG. 1 is a basic structural diagram of an SAS diagnostic apparatus according to the present invention.
Figure 2:
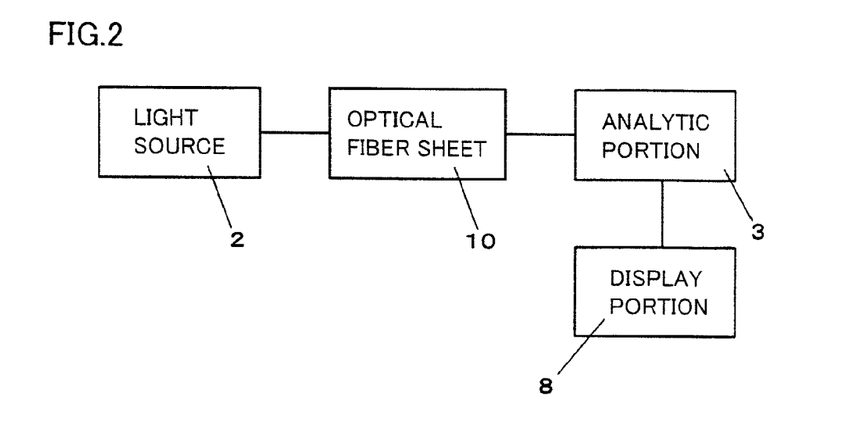
FIG. 2 is a block diagram of the SAS diagnostic apparatus shown in FIG. 1.
Figure 3:
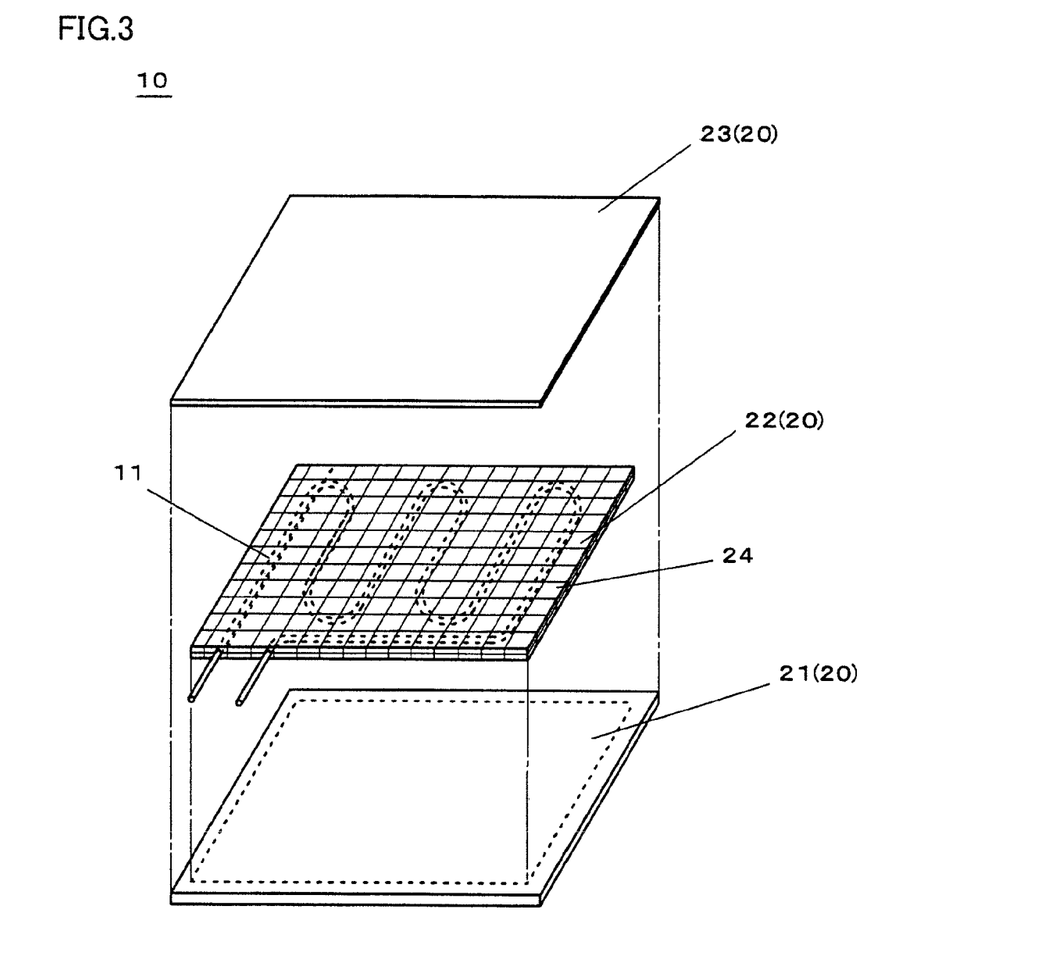
FIG. 3 is an exploded structural diagram of an optical fiber sheet according to an embodiment of the present invention.
Figure 4:
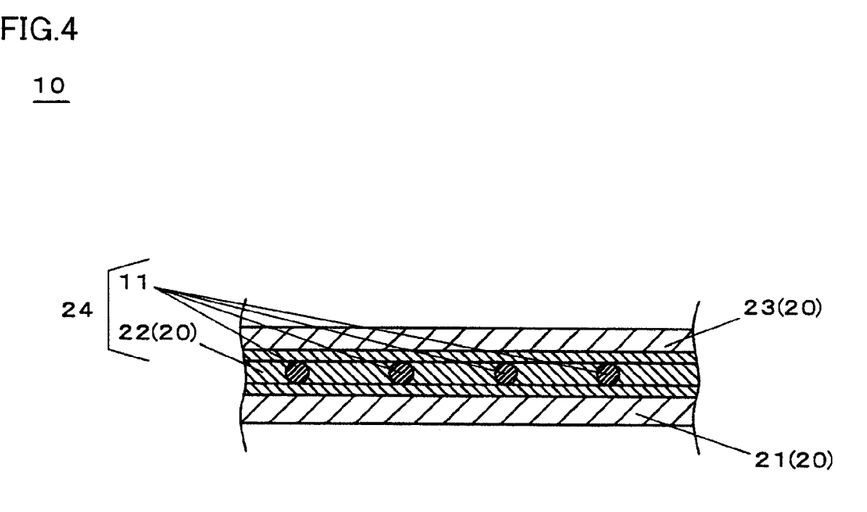
FIG. 4 is a sectional structural diagram of the optical fiber sheet shown in FIG. 3.

FIG. 1 is a basic structural diagram of a sleep apnea syndrome diagnostic apparatus (hereinafter referred to as "SAS diagnostic apparatus") according to the present invention, FIG. 2 is a block diagram of the SAS apparatus, FIG. 3 is an exploded perspective view of an optical fiber sheet according to an embodiment of the present invention employed for the SAS diagnostic apparatus, and FIG. 4 is a sectional structural diagram thereof.

The SAS diagnostic apparatus includes a light source 2, an optical fiber sheet 10 according to the present invention, an analytic portion 3 measuring a change in the quantity of light output from optical fiber sheet 10 and detecting a body motion and a display portion 8 displaying results of the measurement in analytic portion 3. Analytic portion 3 of the SAS diagnostic apparatus shown in FIG. 1 has an actinometer 4 measuring the quantity of light transmitted through optical fiber 11 and a processor 5 detecting fluctuation in the measured light quantity. Optical fiber sheet 10 is arranged on a bed 1 as shown in FIG. 1, for example.

The SAS diagnostic apparatus measures fluctuation in the quantity of light caused by passing through optical fiber 11 and determines whether the subject has a body motion in an apnea state or in a hypopnea state or has a body motion, unrelated to respiration, in a state making a heartbeat or turning over while sleeping in bed, for example, from the fluctuation.

Light source 2 continuously supplies light of a constant quantity to optical fiber 11. The type and the structure of light source 2 are not particularly restricted so far as light source 2 is capable of emitting light of the constant quantity, and a semiconductor light-emitting device such as an LED or an illuminant such as an incandescent body is illustrated. Light source 2 may be either light source 2 pulsingly outputting light in a short cycle or light source 2 continuously outputting light. In order to examine a body motion in sleeping, light source 2 capable of uninterruptedly outputting light during sleeping hours of a human, preferably about eight to 12 hours is desirably employed. In said light source 2, the LED is suitably employed in consideration of that the same can stably output outgoing light, is lightweight and miniature, and exhibits a small heat value and power consumption. In a case of employing an LED light source, the wavelength thereof is desirably that of visible light. This is because disconnection can be easily found by leakage of light. Light source 2 shown in FIG. 1 is formed by an LED, and connected to a USB port of a personal computer employed as processor 5, to be supplied with power through the USB port.

Actinometer 4 includes a photoreceiving device such as a photodiode (PD), for example, and continuously receives the light output from optical fiber 11. Actinometer 4 converts the received light to an electric signal, and outputs the same to processor 5 as the electric signal through a cable 7. Light passing through a core layer of optical fiber 11 may be measured, and reflected light reflected on a boundary surface between the core layer and a cladding layer can also be measured.

Figure 5:
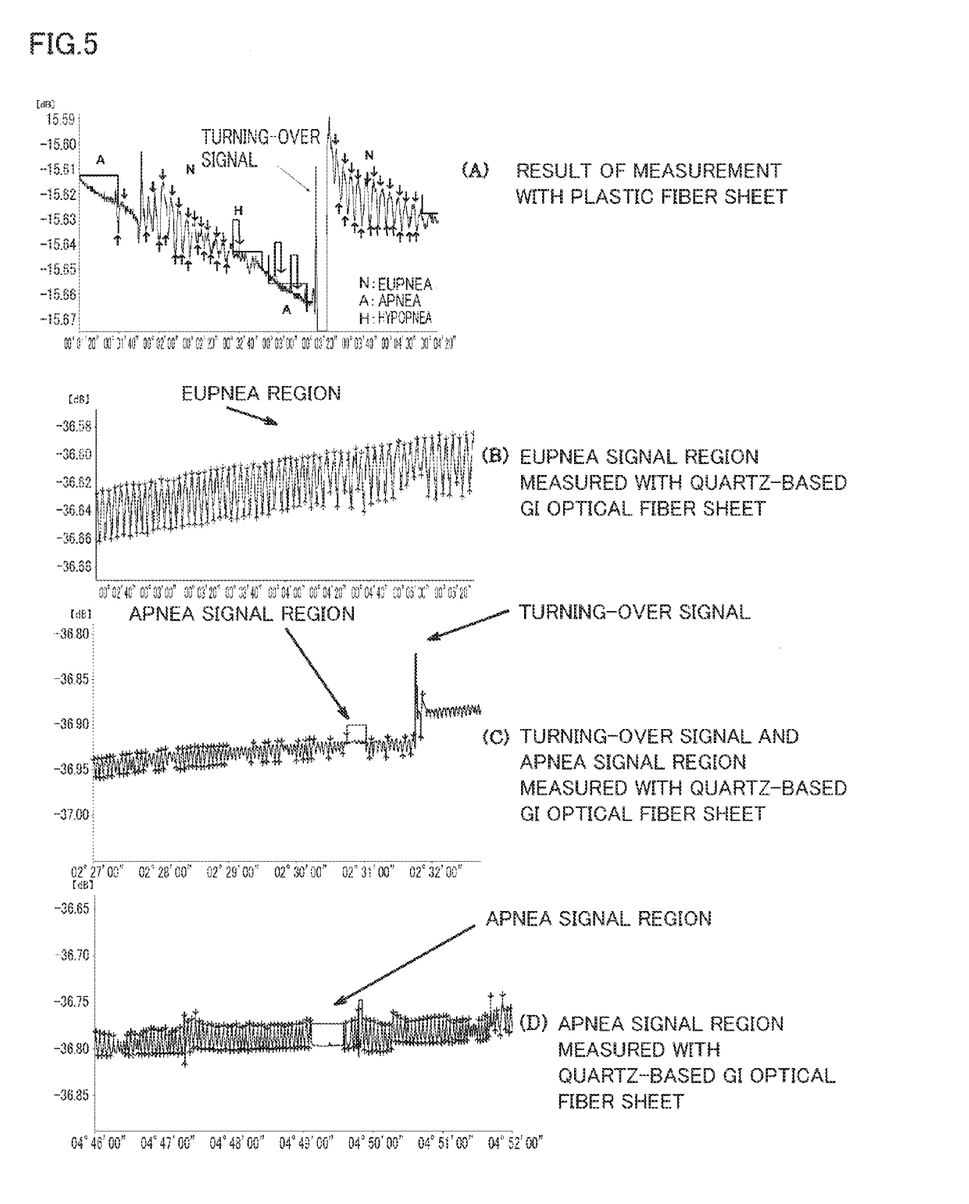
FIG. 5 illustrates examples of measurement results with the SAS diagnostic apparatus having the structure shown in FIG. 1, and (A) shows a measurement result with optical fiber made of plastic according to comparative example, while (B), (C) and (D) show measurement results with GI quartz-based optical fiber. (B) shows a eupnea signal region, (C) shows an apnea signal region and a turning-over signal, and (D) shows an apnea signal region.

Processor 5 obtains a change in the quantity of received light on the basis of the electric signal output from actinometer 4. This change in the received light (quantity of attenuation) is substantially in proportional relation to a lateral pressure applied to optical fiber 11 in response to the body motion, i.e., a motion of the body. In other words, it can be determined that the body motion is small when the change in the quantity of received light is small, and that the body motion is large when the change in the quantity of received light is large. FIG. 5 illustrates graphs showing examples of results of measurement with this diagnostic apparatus. For example, it can be determined that the subject is in an ordinary respiration state (eupnea region) when the quantity of received light regularly changes and is observed with a magnitude of an amplitude of at least a constant quantity, as shown in FIG. 5(B). Further, it can be determined that the subject is in an apnea state when a change in the quantity of received light is hardly observed and a fluctuation amplitude is small as shown in FIG. 5(C) or (D). In addition, it can be determined that the subject is in a hypopnea state when the change in the quantity of received light is between the ordinary respiration state and the apnea state. When a change remarkably larger than the change in the ordinary respiration state is observed, it can be determined that the same results from that the subject has remarkably moved his/her body by turning over or the like (see FIG. 5(C)). These measurement results are displayed on display portion 8 such as a liquid crystal panel provided on the personal computer.

Optical fiber sheet 10 is constituted of graded index quartz-based optical fiber 11 (quartz-type GI optical fiber 11) and a planar body 20 supporting the same. Quartz-type GI optical fiber 11 is optical fiber 11 whose refractive index has refractive index distribution (Graded Index) having a central axisymmetric distribution shape from the center of a core to a clad direction, in which both of the core and the clad are made of quartz glass.

Microbending loss is caused in GI quartz-based optical fiber 11 by stress loading resulting from the lateral pressure, and excess loss is caused in transmission loss of optical fiber 11. The present invention utilizes this characteristic, and renders the body motion measurable by measuring a change in the excess loss resulting from a change in stress loading on optical fiber 11 by the body motion. In other words, the excess loss varied with the body motion is obtained by a change in the quantity of light passed through optical fiber 11. Particularly quartz-type GI optical fiber 11 is extremely sensitive to the lateral pressure, and exhibits large excess loss in the case where stress loading resulting from the lateral pressure takes place. In particular, GI optical fiber can include and transmit a large quantity of a higher-order mode (light propagating also through a portion close to a clad side more separated from a core center) easily causing microbending loss, whereby a remarkable light quantity change can be caused with merely a slight body motion. However, this higher-order mode is more remarkably influenced by absorption of the core than a lower-order mode (light having high linearity propagating through a core central portion in a larger quantity), and hence the higher-order mode is attenuated in an intermediate stage and cannot be utilized if absorption of the material for the core itself is large. In order to efficiently utilize the higher-order mode, therefore, a material exhibiting minimum absorption is advantageously employed as the material for the core. Quartz is a material having the smallest absorption loss among materials generally used for optical fiber, and hence it can be said that the same is most suitable for this use.

In order to maximize sensitivity to the body motion, an input state of signal light is desirably so controlled that light of a higher-order mode is propagated to the GI quartz-based optical fiber in the largest quantity. Such a condition is referred to as a total mode excitation condition. This condition is attained when the diameter (or the numerical aperture) of the light source is larger than the diameter (or the numerical aperture) of the optical fiber in relation to the diameter or the aperture number of the light source inputting light into the optical fiber. This condition can be attained by employing an LED light source having an aperture number larger than the aperture number of the used GI quartz-based optical fiber as the light source, for example.

Thus, when utilizing the GI quartz-based optical fiber in a higher-order mode by inputting light particularly under a total mode excitation condition, a remarkable light quantity change is caused with only a slight body motion. Consequently, measurement with remarkably excellent sensitivity becomes possible. Further, a measurement result hardly influenced by electrical noise of static electricity resulting from friction or the like and causing small misidentification can be obtained.

In the GI quartz-based optical fiber, the sectional shape of the fiber is completely isotropic and no bending direction dependence is present in bending loss, whereby directions of fiber may not be aligned in formation of the optical fiber sheet, and it can be said that the same is more advantageous as compared with the optical fiber sheet disclosed in Patent Document 1 also in this potent. Further, the quartz-based optical fiber has extremely high rigidity as compared with fiber made of, whereby deterioration of characteristics resulting from kinking or the like is hardly caused when the same is fixed to the optical fiber sheet, and the same is excellent in productivity. In addition, the fiber is neither deformed nor crushed also when the same is used in a loaded state over a long period, whereby the same is excellent in long-term stability. While there is also fiber employing multi-component glass as optical fiber excellent in rigidity, on the other hand, the quartz-based optical fiber is widely utilized for a communication use, and hence the same is excellent also in points that the same is easy to obtain, has stable performance and exhibits high weather resistance. Thus, the GI quartz-based optical fiber is extremely advantageous also in view of manufacturing of the optical fiber sheet.

Planar body 20 performs a function of supporting optical fiber 11. For planar body 20, not only that referred to as the so-called cloth, whether the same is woven cloth, knitted cloth or nonwoven cloth, but also any sheetlike one such as a plastic sheet, paper or a net having a mesh structure can be utilized. Further, planar body 20 is employed in a wide concept including not only a sheetlike one such as the aforementioned cloth or the plastic sheet, but also bedding itself such as a mattress having a core of a spring structure or a sponge structure, a futon or a blanket, planar body 20 such as a sponge body employed for a mattress or a futon directly utilizable as bedding, planar body 20 workable into bedding with such a material and the like.

In order to simplify manufacturing steps for optical fiber sheet 10, an adhesive sheet or an adhesive tape is employed as described later. This adhesive sheet or the adhesive tape is prepared by forming a support by any sheetlike object such as cloth, paper or a plastic sheet and providing an adhesive layer on one surface or each surface of the support. In the present invention, the support employed for this adhesive sheet or the adhesive tape can also be utilized as planar body 20.

The material for planar body 20 (including the support such as the adhesive sheet) is not particularly restricted. As a material of cloth, natural fiber such as silk, cotton, hemp or wool, regenerated fiber such as acetate or rayon or synthetic fiber such as nylon, polyurethane or polyester is illustrated, for example. As a material for the plastic sheet, polyethylene, polyurethane, acrylonitrile butadiene styrene (ABS), ethylene propylene rubber, vinyl chloride, thermoplastic elastomer such as styrene-butadiene-based, olefin-based (TPO), polyester-based (TPEE) or polyurethane-based (TPU) elastomer, polyamide, polyurethane, polypropylene or expanded polystyrene is illustrated.

Among these, a flexible material is suitably employed. Further, air-permeable planar body 20 such as a porous sponge sheet or knitted cloth consisting of cotton or wool is more desirably employed for planar sheet 20. This is because optical fiber sheet 10 according to the present invention is employed as bedding such as a mattress, a bed or a futon or a sort of a bed sheet or an under-blanket spread on such bedding, and can avoid influence by perspiration or the like in sleeping. Further, a wood plate or the like can also be utilized as the case may be.

Optical fiber 11 is directly or indirectly arranged on planar body 20 in the form of a meandering one-stroke sketch. Optical fiber 11 is not only arranged on aforementioned planar body 20 serving as a support substrate, but can also be knitted into planar body 20, embedded in planar body 20, or arranged on a laminate of planar body 20. Further, optical fiber 11 is arranged by a method of holding the same between two planar bodies 20 or holding the same between laminates consisting of a plurality of planar bodies 20.

GI quartz-based optical fiber 11 generally has a coating for maintaining strength. Therefore, there is no apprehension that the same is influenced by external light, i.e., stray light. An outer cover can also be arbitrarily provided. In this case, it is also possible to select that of a free pattern or coloration, and when the outer cover is rendered detachable, for example, only the outer cover can be detached and washed, so that consideration in a sanitary point of view is also possible.

As a method of arranging and fixing optical fiber 11 on and to planar body 20, optical fiber 11 can also be directly arranged on and fixed to planar body 20 with an adhesive or the like. Further, optical fiber 11 can also be arranged between and fixed to two planar bodies 20 by holding upper and lower portions of optical fiber 11 with planar bodies 20, bringing planar bodies 20 into pressure contact with each other and vapor-depositing or bonding the peripheral edges thereof. Optical fiber 11 may also be embedded in cotton of a futon, to be indirectly arranged on and fixed to planar body 20.

Further, optical fiber 11 can be indirectly arranged on and fixed to planar body 20 with an adhesive sheet or an adhesive tape having an adhesive layer formed on a support such as paper or a plastic sheet. In addition, a method of placing optical fiber 11 on planar body 20 and fixing the same with an adhesive sheet or an adhesive tape from above the same or the like can be illustrated.

Optical fiber sheet 10 shown in FIGS. 3 and 4 is constituted of an air-permeable sponge sheet 21 having a large number of holes, a mesh structure 24 in which optical fiber 11 is knitted into knitted cloth 22 of a mesh structure and a black cloth cover 23 having a light-shielding property, and has such a structure that mesh structure 24 is held between sponge sheet 21 and cloth cover 23. The peripheral edges of sponge sheet 21 and cloth cover 23 are sewn up together, to prepare optical fiber sheet 10. Optical fiber sheet 11 is arranged in the form of a one-stroke sketch having six columns of arranged portions parallel to the short sides of optical fiber sheet 10.

FIG. 5 illustrates examples showing results actually measured with the SAS diagnostic apparatus having the structure shown in Example 1. In this measurement, an optical fiber sheet was held and arranged between a futon and a bed sheet spread thereon. An optical fiber sheet (see FIGS. 3 and 4) includes a 3-mm thick sponge sheet having a large number of pores, an air-permeable knitted cloth of a mesh structure provided thereon, an optical fiber (core diameter $\phi$ of 50 μm, a clad diameter $\phi$ of 125 μm, and arrangement extension of 7 m) woven in the knitted cloth as shown in FIG. 3, and a cover made of black cloth further placed on this mesh structure. A light source for USB connection of an output employing a red LED was employed for a light source. The light source and an incidence end of the optical fiber sheet as well as an outgoing end of the optical fiber sheet and an optical power meter were optically connected with each other with POF (Plastic Optical Fiber) respectively. An output from the optical power meter was data-processed with a personal computer, to calculate a light quantity change. The subject is a male of 175 cm in height and 85 kg in weight, exhibiting a BMI of 27.8, 43 years old. It was reported from his mate that he snored loudly in everyday sleeping and was suspected of a respiratory arrest at midnight. With the cooperation of the subject, therefore, measurement was performed under the same conditions as those in usual sleeping in the residence of the subject.

The axes of ordinates and the axes of abscissas in FIG. 5 show quantities (absolute values) of light received from the optical fiber sheet and elapsed times respectively. Changes in the quantities of received light are extremely small in apnea signal regions in FIG. 5, while a remarkable change is recognized in the quantity of received light in a eupnea region. Further, such a remarkable change in the quantity of received light that the amplitude overshot was observed in addition to these regions. As obvious also from FIG. 5, a body motion in the eupnea region and body motions in the apnea signal regions are clearly distinguished from each other. Thus, not only an apnea state and a eupnea state can be clearly read, but also a hypopnea state present therebetween can also be clearly read. Further, it has been confirmed that the measurement is not influenced by stray light, but is effective also in a case where there is night illumination. In the example employing the plastic fiber, the graph is descending as a whole along with the elapsed time. This is conceivably because loss changed due to deformation of the fiber itself over time caused by a load since the plastic fiber is soft. In the case of employing the GI quartz-based optical fiber, on the other hand, no phenomenon resulting from deformation was observed.

When measurement was performed on 10 subjects of ages 35 to 82 from a lean female (weight: 42 kg) to a fat male (weight: 85 kg) with the aforementioned SAS diagnostic apparatus in addition to this subject, it was possible to screen six subjects whose Provisional-AHI (RDI-corresponding) indices (apnea-hypopnea indices) were at least 5. When the subjects except the one for whom it was difficult to undergo an overnight test in the hospital for certain reasons were made to have PSG tests in a special medical facility for definitive diagnosis, such definitive diagnostic results were obtained that the AHI indices of the remaining five subjects were distributed in the range of 5 to 40.

Thus, with the SAS diagnostic apparatus according to the present invention, it was possible to simply perform measurement also in a general home. Further, it has been clarified that noninvasive and nonrestraint measurement is possible identically to a sleeping state similar to general sleeping without wearing a specific apparatus when this apparatus is used, and the apparatus is extremely effective for screening a potential patient having a high possibility of being a patient of SAS syndrome. It has also been clarified that measurement can be performed also in a bright room without being influenced by stray light.

EXAMPLE 2

Figure 6:
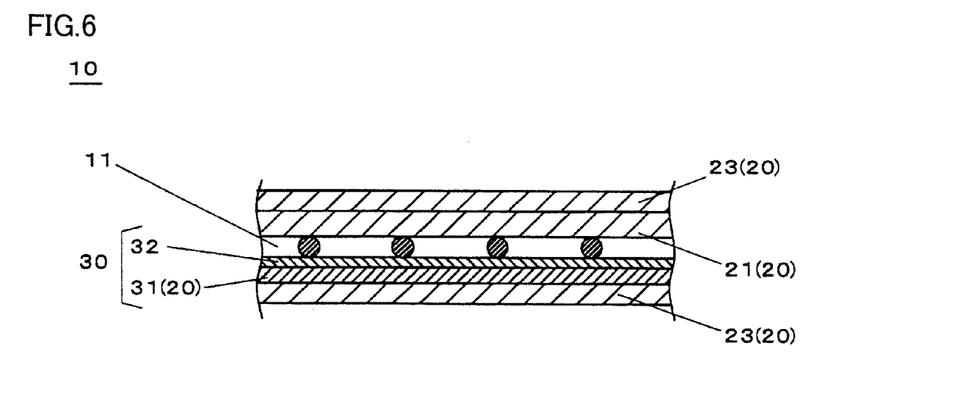
FIG. 6 is a sectional structural diagram of an optical fiber sheet according to another embodiment of the present invention.

FIG. 6 is a sectional structural diagram of an optical fiber sheet 10 according to another embodiment of the present invention. Optical fiber sheet 10 has optical fiber 11, an adhesive sheet 30 having an adhesive layer 32 substantially on the whole surface of a support 31, a sponge sheet 21 and outer covers 23, made of cloth, having a light shielding property. Optical fiber 11 is arranged on and fixed to adhesive layer 32, and sponge sheet 21 is superposed thereon. The upper and lower surfaces of these are covered with outer covers 23 respectively. Optical fiber sheet 10 exhibits a similar function to optical fiber sheet 10 shown in FIG. 3, and attains such an advantage that productivity further improves rather in a point that meandering optical fiber is arranged on whole surface adhesive sheet 30.

EXAMPLE 3

Figure 7:
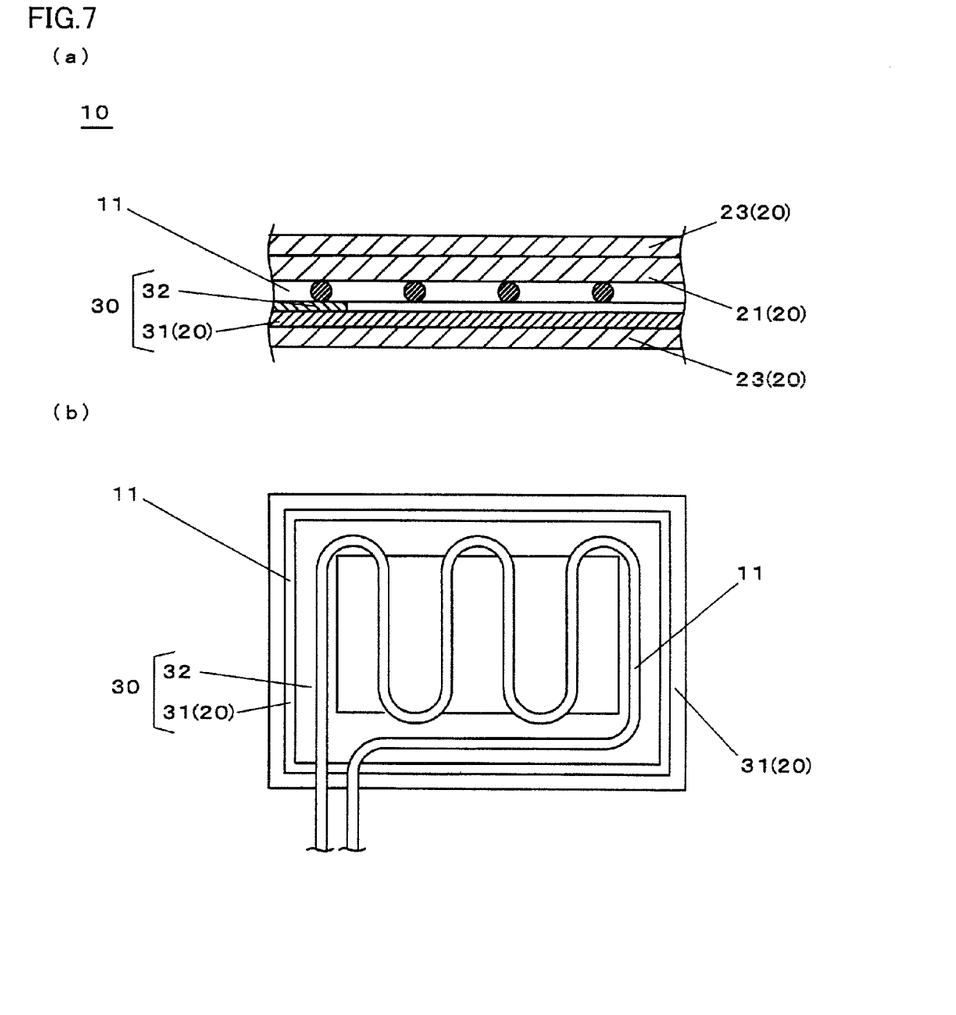
FIG. 7 illustrates the structure of an optical fiber sheet according to still another embodiment of the present invention, and (a) in FIG. 7 is a sectional structural diagram thereof, while (b) in FIG. 7 is a partially omitted plan view thereof.
Figure 8:
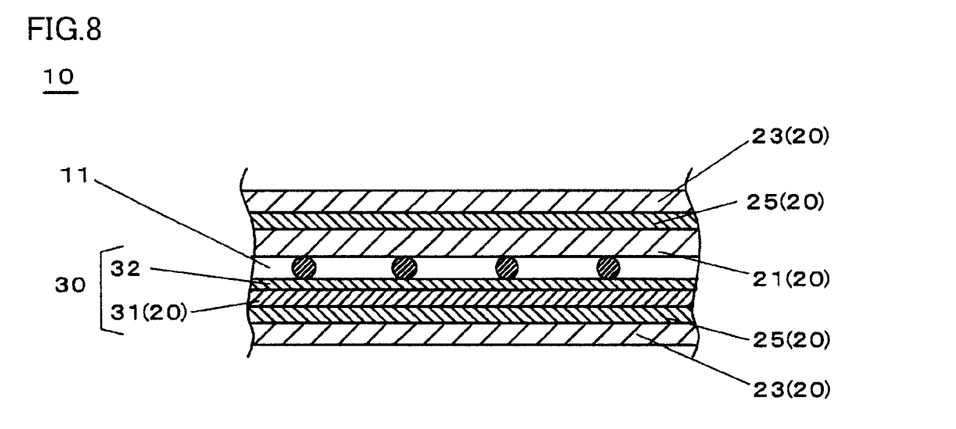
FIG. 8 is a sectional structural diagram of an optical fiber sheet according to a further embodiment of the present invention.

FIG. 7(a) is a sectional structural diagram of an optical fiber sheet 10 according to still another embodiment of the present invention, and FIG. 7(b) is a partially omitted plan view of optical fiber sheet 10. Optical fiber sheet 10 shown in FIG. 7 has optical fiber 11, an adhesive tape 30 having an adhesive layer 32 on the peripheral edge of a surface of a sheetlike support 31, a sponge sheet 21 and outer covers 23, made of cloth, having a light shielding property. Optical fiber 11 is arranged on and fixed to adhesive sheet 30, and sponge sheet 21 is superposed thereon. The upper and lower surfaces of these are covered with outer covers 23 respectively. As shown in FIG. 8, an optical fiber sheet 10 including inner covers 25 made of knitted cloth having mesh structures respectively inside upper and lower covers 23 made of cloth to have a double-cover structure of inner covers 25 and outer covers 23 was prepared. These optical fiber sheets 10 exhibit similar functions to optical fiber sheet 10 shown in FIG. 3, and attain such an advantage that productivity further improves in a point that meandering optical fiber is arranged on peripheral (four-side) adhesive sheet 30.

EXAMPLE 4

In the present invention, not only adhesive sheet 30 (see FIG. 7 or FIG. 8) having adhesive layer 32 only on the peripheral edge of support 31, but an adhesive sheet 30 partially having an adhesive layer 32 on a surface of a support 31 as in Example described below can be used. This is because arrangement of optical fiber 11 is simplified due to the utilization of adhesive sheet 30.

Figure 9:
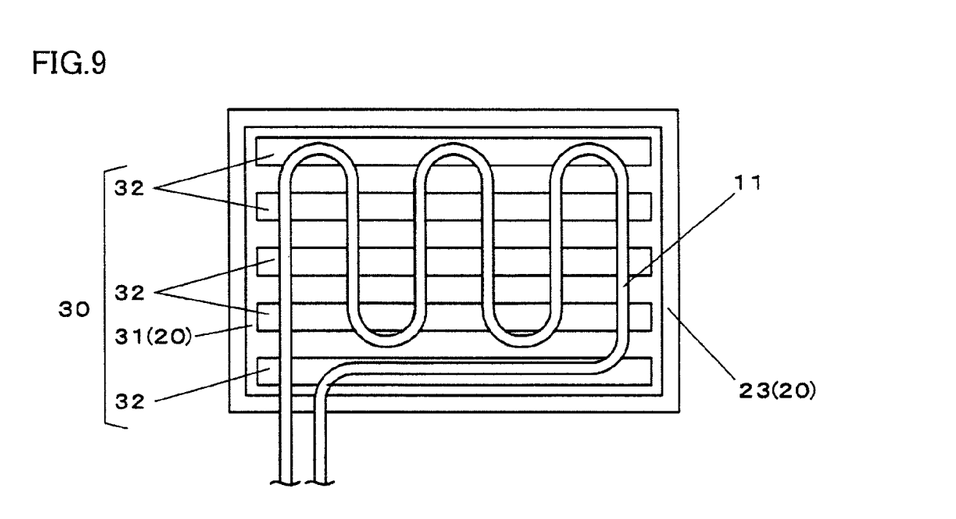
FIG. 9 is a partially omitted plan view of an optical fiber sheet according to a further embodiment of the present invention.

FIG. 9 is a partially omitted plan view of an optical fiber sheet 10 according to a further embodiment of the present invention. While optical fiber sheet 10 shown in FIG. 9 has a structure substantially similar to that of optical fiber sheet 10 shown in FIG. 7, an adhesive sheet 30 in which adhesive layers 32 are provided in the form of stripes parallel to a long-axis direction of a support 31 is employed on a surface of sheetlike support 31 in optical fiber sheet 10 shown in FIG. 9.

Also in optical fiber sheet 10, optical fiber 11 is arranged on and fixed to adhesive sheet 30 having adhesive layers 32 in the form of stripes, and a sponge sheet 21 is arranged thereon. Thus, adhesive sheet 30 provided with adhesive layers 32 in the form of stripes can also be employed. Optical fiber sheet 10 also exhibits a similar function to optical fiber sheet 10 shown in FIG. 3, and attains such an advantage that productivity further improves in a point that meandering optical fiber is arranged on striped adhesive sheet 30 Inner covers 25 made of knitted cloth of mesh structures may further be arranged as shown in FIG. 8, so that optical fiber sheet 10 has a double-cover structure of inner covers 25 and outer covers 23 (not shown), as a matter of course.

Figure 10:
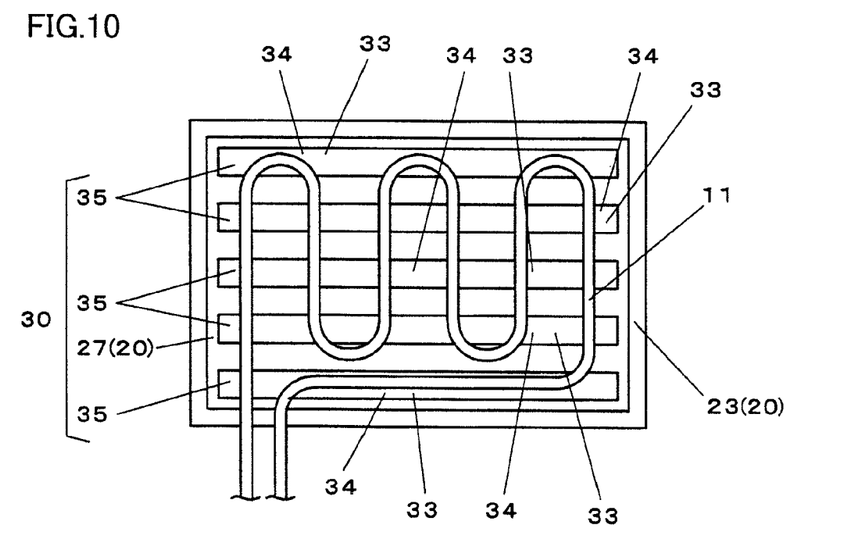
FIG. 10 is a partially omitted plan view of an optical fiber sheet according to a further embodiment of the present invention.

In an optical fiber sheet 10 shown in FIG. 10, an adhesive sheet 30 in which adhesive tapes (the so-called double-faced adhesive tapes) 35 having adhesive layers 34 formed on both surfaces of tapelike supports 33 are stuck to a planar body 27 of paper is employed as the substitution of striped adhesive sheet 30. Such employment of double-faced adhesive tapes 35 also becomes an effective means.

EXAMPLE 5

Figure 11:
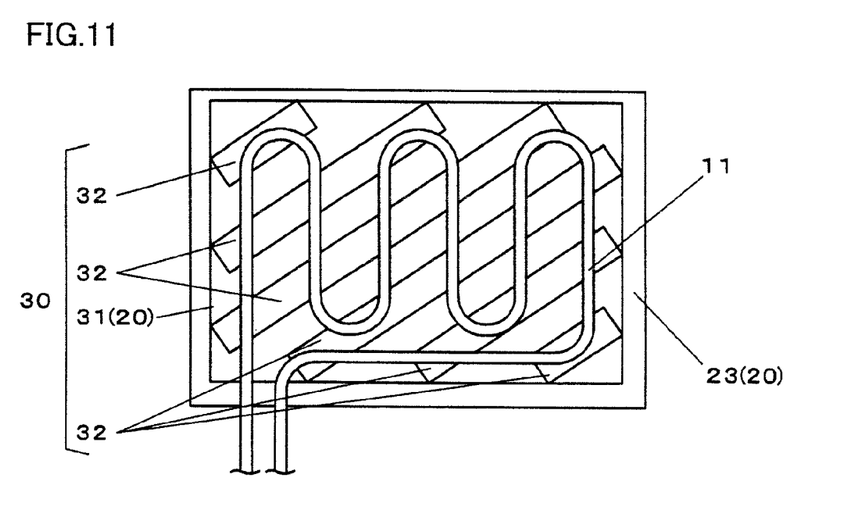
FIG. 11 is a partially omitted plan view of an optical fiber sheet according to a further embodiment of the present invention.

FIG. 11 is a partially omitted plan view of an optical fiber sheet 10 according to a further embodiment of the present invention. While optical fiber sheet 10 also has a similar structure to optical fiber sheet 10 shown in FIG. 7, an adhesive sheet 30 in which adhesive layers 32 are provided in the form of oblique stripes on a surface of a sheetlike support 31 is employed in optical fiber sheet 10 shown in FIG. 11. Optical fiber sheet 10 also exhibits a similar function to of optical fiber sheet 10 shown in FIG. 3, and attains such an advantage that productivity further improves rather in a point that meandering optical fiber is arranged on obliquely striped adhesive sheet 30. Inner covers 25 made of knitted cloth of mesh structures may further be arranged similarly to optical fiber sheet 10 shown in FIG. 8, so that optical fiber sheet 10 has a double-cover structure of inner covers 25 and outer covers 23 (not shown), as a matter of course.

Although not shown, it is also an effective means to employ adhesive sheet 30 in which adhesive tapes (the so-called double-faced adhesive tapes) 35 having adhesive layers 34 formed on both surfaces of tapelike supports 33 are stuck to planar body 27 of paper as the substitution of obliquely striped adhesive sheet 30.

EXAMPLE 6

Figure 12:
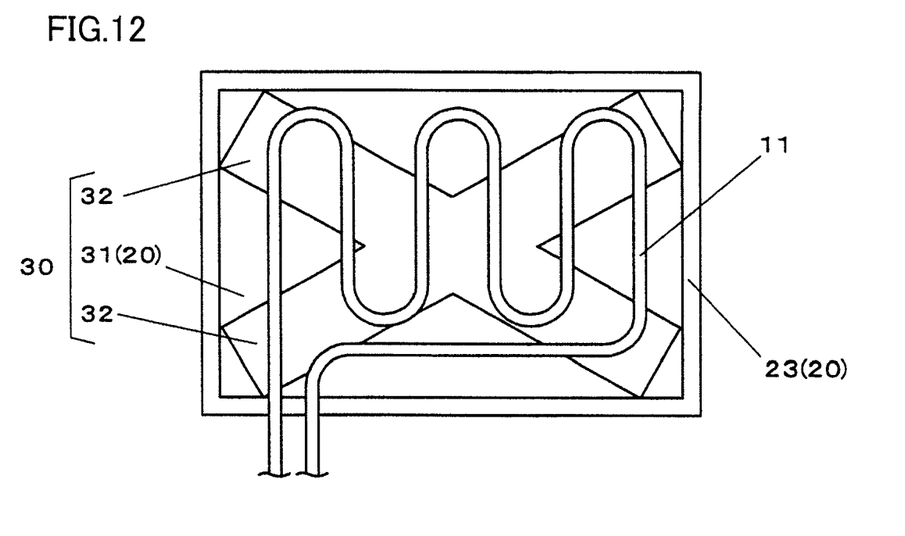
FIG. 12 is a partially omitted plan view of an optical fiber sheet according to a further embodiment of the present invention.

FIG. 12 is a partially omitted plan view of an optical fiber sheet 10 according to a further embodiment of the present invention. While optical fiber sheet 10 has a similar structure to optical fiber sheet 10 shown in FIG. 7, optical fiber sheet 10 shown in FIG. 12 is different in a point that an adhesive sheet 30 in which adhesive layers 32 are provided in the form of an oblique cross on a surface of a sheetlike support 31 is employed. Such adhesive sheet 30 having adhesive layers 32 provided in the form of oblique stripes can also be employed. Optical fiber sheet 10 also exhibits a similar function to optical fiber sheet 10 shown in FIG. 3, and attains such an advantage that productivity further improves in a point that meandering optical fiber is arranged on adhesive sheets 30 in the form of the oblique cross. Inner covers 25 made of knitted cloth of mesh structures may further be arranged similarly to optical fiber sheet 10 shown in FIG. 8, so that optical fiber sheet 10 has a double-cover structure of inner covers 25 and outer covers 23 (not shown), as a matter of course.

EXAMPLE 7

Figure 13:
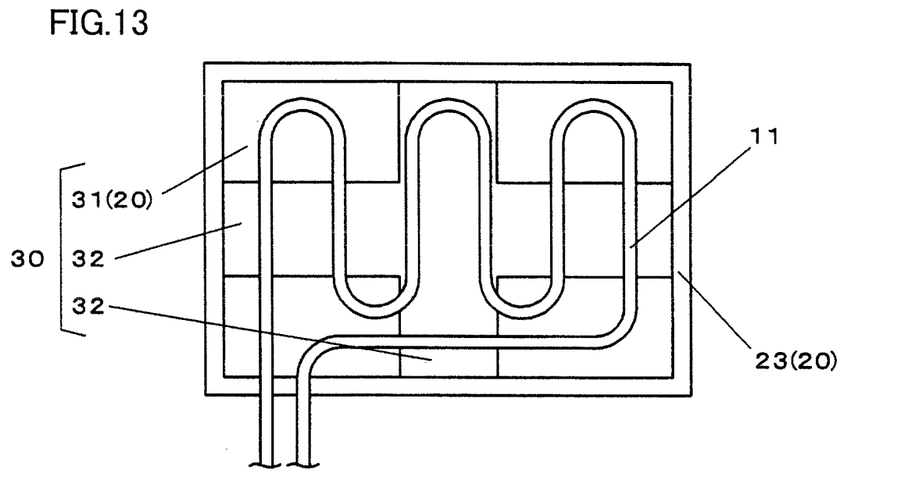
FIG. 13 is a partially omitted plan view of an optical fiber sheet according to a further embodiment of the present invention.

FIG. 13 is a partially omitted plan view of an optical fiber sheet 10 according to a further embodiment of the present invention. While optical fiber sheet 10 has a similar structure to optical fiber sheet 10 shown in FIG. 7, an adhesive sheet 30 in which adhesive layers 32 are provided in the form of a cruciform cross on a surface of a sheetlike support 31 is employed in optical fiber sheet 10 shown in FIG. 13. Such adhesive sheet 30 having adhesive layers 32 provided in the form of the cruciform cross can also be employed.

Although not shown, an adhesive sheet 30 in which the so-called double-faced adhesive tapes are stuck to a planar body 27 of paper in the form of an oblique cross or a cruciform cross can be employed in place of adhesive sheet 30 in which adhesive layers 32 are provided in the form of the oblique cross or the cruciform cross also in Example 6 or Example 7, as a matter of course.

EXAMPLE 8

Figure 14:
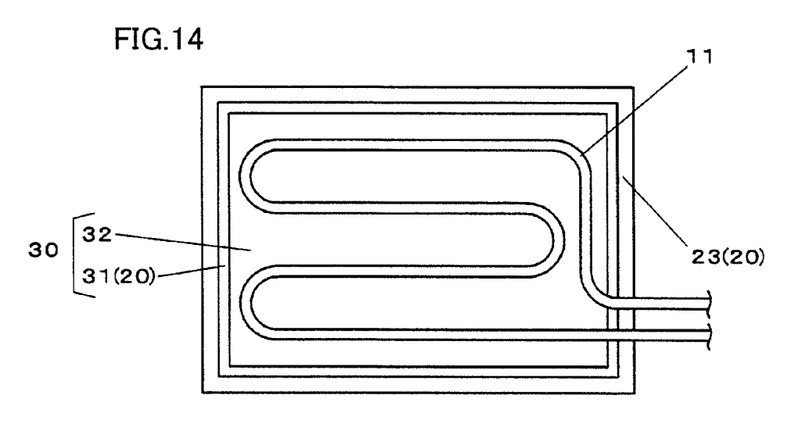
FIG. 14 is a partially omitted plan view of an optical fiber sheet according to a further embodiment of the present invention.

FIG. 14 is a partially omitted plan view of an optical fiber sheet 10 according to a further embodiment of the present invention. While optical fiber sheet 10 has a similar structure to optical fiber sheet 10 shown in FIG. 3, optical fiber 11 is arranged in a direction (the so-called vertical direction) parallel to the long sides of optical fiber sheet 10, and arranged portions parallel to the long sides of optical fiber sheet 10 are present in a plurality of columns in optical fiber sheet 10 shown in FIG. 14. A body motion can be detected also when arranging optical fiber 11 in the direction parallel to the long sides of optical fiber sheet 10 in this manner.

EXAMPLE 9

Figure 15:
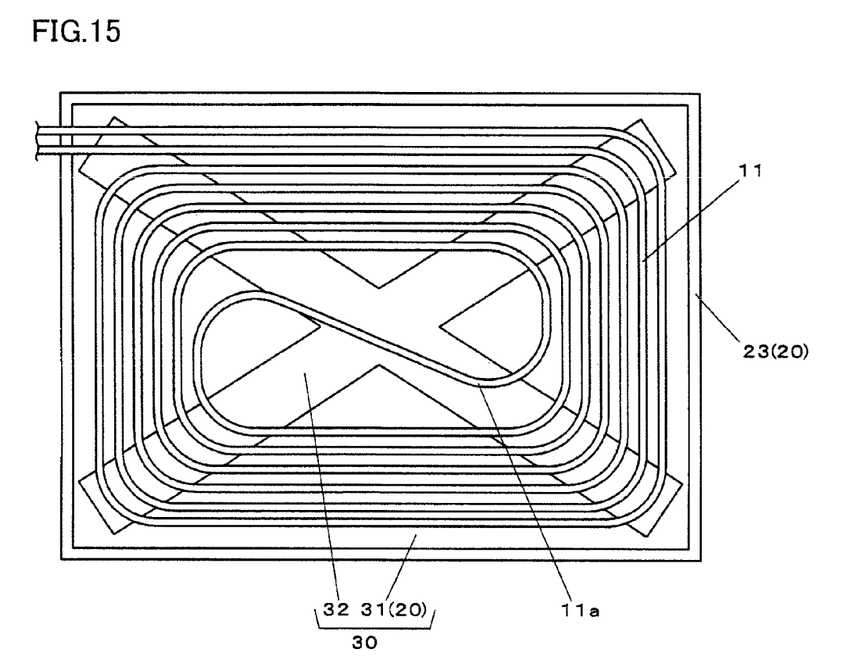
FIG. 15 is a partially omitted plan view of an optical fiber sheet according to a further embodiment of the present invention.

FIG. 15 is a partially omitted plan view of an optical fiber sheet 10 according to a further embodiment of the present invention. While optical fiber sheet 10 has a similar structure to the optical fiber sheet shown in FIG. 12, optical fiber 11 is arranged in a spiral shape having a turn portion 11a on a substantially central region of an adhesive sheet 30 so that the arrangement length of optical fiber 11 increases. Turn portion 11a is a folded portion of optical fiber 11 arranged in the fin in of a one-stroke sketch. A change in the quantity of received light enlarges and detection sensitivity rises as the arrangement length of optical fiber 11 increases. It can be said that the spiral arrangement, increasing the arrangement length per unit area, is a more preferable embodiment.

While optical fiber sheet 10 according to the present invention can detect a body motion of a person on a dorsal position or a prone position and hence the same is extremely suitable for diagnosing SAS, the same is not necessarily restricted to the SAS diagnostic apparatus, but can be widely employed for an apparatus for detecting a body motion and catching movement of a posture in addition to the SAS diagnostic apparatus, as a matter of course.

The embodiments and Examples shown in the above are illustrations and the present invention is not restricted to the aforementioned embodiments and Examples, but it is intended that all modifications in the range of the scope of claims for patent and included equivalently thereto are included in the present invention.

REFERENCE SIGNS LIST 1 bed
2 light source
3 analytical portion
4 actinometer
5 processor
10 optical fiber sheet
11 optical fiber
20 planar body
21 sponge sheet which is planar body
23 outer cover which is planar body
24 mesh structure into which optical fiber is knitted
30 adhesive sheet
31 support (planar body) for adhesive sheet
35 double-faced adhesive tape

The invention claimed is:

1. A body motion sensor comprising:
an optical fiber sheet comprising optical fiber and a planar body, for measuring a change in the quantity of transmission signal light based on excess loss caused by a lateral pressure applied to the optical fiber; and
a light source configured to supply light to said optical fiber, wherein
said optical fiber is graded index quartz-based optical fiber,
said light source is a red LED,
input signal light into the optical fiber is input under a total mode excitation condition, and
a numerical aperture of said light source is larger than a numerical aperture of said optical fiber,
the optical fiber is arranged through an adhesive layer on a sheetlike support and the adhesive layer covers a partial area of the surface of the sheetlike support,
the light source having a diameter, and the optical fiber having a diameter, and
the diameter of the light source is larger than the diameter of the optical fiber.

2. The body motion sensor according to claim 1, wherein said optical fiber sheet is characterized in that said optical fiber is arranged on said adhesive sheet having an adhesive layer substantially on the whole region of the surface of the sheetlike support.

3. The body motion sensor according to claim 1, wherein said optical fiber sheet is characterized in that said optical fiber is arranged on said adhesive sheet having an adhesive layer on the peripheral edge of the surface of the sheetlike support.

4. The body motion sensor according to claim 1, wherein said optical fiber sheet is characterized in that said optical fiber is arranged on said adhesive sheet having adhesive layers provided in the form of stripes on the surface of the sheetlike support.

5. The body motion sensor according to claim 1, wherein said optical fiber sheet is characterized in that said optical fiber is arranged on said adhesive sheet having adhesive layers provided in the form of oblique stripes on the surface of the sheetlike support.

6. The body motion sensor according to claim 1, wherein said optical fiber sheet is characterized in that said optical fiber is arranged on said adhesive sheet having adhesive layers provided in the form of a cruciform cross on the surface of the sheetlike support.

7. The body motion sensor according to claim 1, wherein said adhesive sheet is formed by sticking a double-faced adhesive tape onto the surface of the sheetlike support.

8. The body motion sensor according to claim 1,
further comprising an analytic portion measuring a change in the quantity of light output from the optical fiber sheet for detecting a body motion.

9. A method of manufacturing an optical fiber sheet comprising graded index quartz-based optical fiber and a planar body, having a step of fixing said optical fiber to an adhesive sheet including an adhesive layer on said planar body, and
inputting signal light into said optical fiber under a total mode excitation condition, wherein
said adhesive sheet has the adhesive layer only on a partial area of a surface of a sheetlike support,
a numerical aperture of said light source is larger than a numerical aperture of said optical fiber,
the light source having a diameter, and the optical fiber having a diameter, and
the diameter of the light source is larger than the diameter of the optical fiber.

* * * * *